Figure 1:
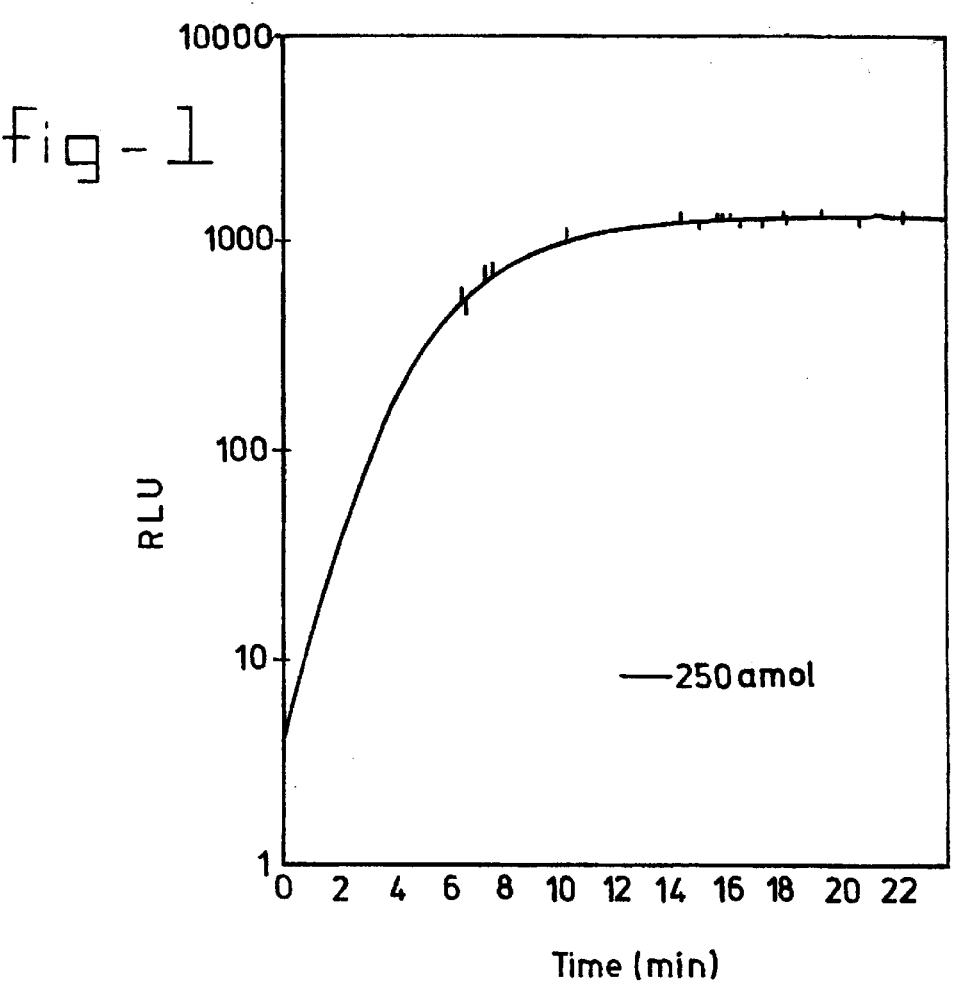

United States Patent [19]

Jacquemijns et al.

[11] Patent Number: 6,030,803
[45] Date of Patent: Feb. 29, 2000

[54] DIBENZODIHYDROPYRIDINECARBOXYLIC ESTERS AND THEIR USE IN CHEMILUMINESCENT ASSAY METHODS

[75] Inventors: Marjorie Jacquemijns, Vleuten; Gijsbert Zomer, Zeist, both of Netherlands

[73] Assignee: De Staat der Nederlanden, vertegenwoordigd door de Minister van Welzijn, Volksgeszonheid en Cultuur, Rijswijk, Netherlands

[21] Appl. No.: 09/214,514

[22] PCT Filed: Jul. 15, 1997

[86] PCT No.: PCT/NL97/00417

§ 371 Date: Jan. 7, 1999

§ 102(e) Date: Jan. 7, 1999

[87] PCT Pub. No.: WO98/02421

PCT Pub. Date: Jan. 22, 1998

[30] Foreign Application Priority Data

Jul. 16, 1996 [EP] European Pat. Off. .............. 96202022

[51] Int. Cl.[7] .............................. C12Q 1/28; C12Q 1/00; G01N 33/53
[52] U.S. Cl. ................................ 435/28; 435/4; 435/968; 435/975; 546/348; 546/351; 560/1; 560/16; 560/20
[58] Field of Search .................................. 435/28, 4, 968, 435/975; 546/348, 351; 560/1, 16, 20

[56] References Cited

U.S. PATENT DOCUMENTS 5,336,772  8/1994  Saiki et al. ............................ 546/289

FOREIGN PATENT DOCUMENTS

| 0 257 541 | 3/1988 | European Pat. Off. . |
| 0 322 926 | 7/1989 | European Pat. Off. . |
| 0 330 433 | 8/1989 | European Pat. Off. . |
| 0 625 510 | 11/1994 | European Pat. Off. . |

OTHER PUBLICATIONS

R.R. Burtner, "Antispasmodics. II. Basic Esters of Some Polynuclear Carboxylic Acids", *Journal of the American Chemical Society*, vol. 65, 1943, pp. 1582–1585. Month not available.

F. McCapra et al., "Chemiluminescence Involving Peroxide Decompositions", *Photochemistry and Photobiology*, vol. 4, 1965, pp.1111–1121. Month not available.

*Primary Examiner*—Louise N. Leary
*Attorney, Agent, or Firm*—Young & Thompson

[57] ABSTRACT

Dibenzodihydropyridinecarboxylic esters are provided which comply with formula (1) or (2), wherein: $R_1$ is substituted alkyl or cyano; $R_2$ and $R_3$ are independently hydrogen, alkyl, substituted alkyl, aryl or substituted aryl; $R_4$ is hydrogen, alkyl, substituted alkyl, aryl or substituted aryl; $R_5$ and $R_6$ are independently alkyl, alkoxy or another substituent which is relatively resistant to oxidation; m and n are integers from 0 to 4; wherein, if m or n is at least 2, two groups $R_5$ or $R_6$ may be linked together; and Z is oxygen or sulphur. The new compounds are used in a method as chemiluminogenic reagents for detecting the presence of peroxidase activity at extremely low levels ($10_{-20}$ moles). A kit containing the dibenzodihydropyridine-carboxylic esters for use in assaying peroxidase activity has also been described.

12 Claims, 3 Drawing Sheets

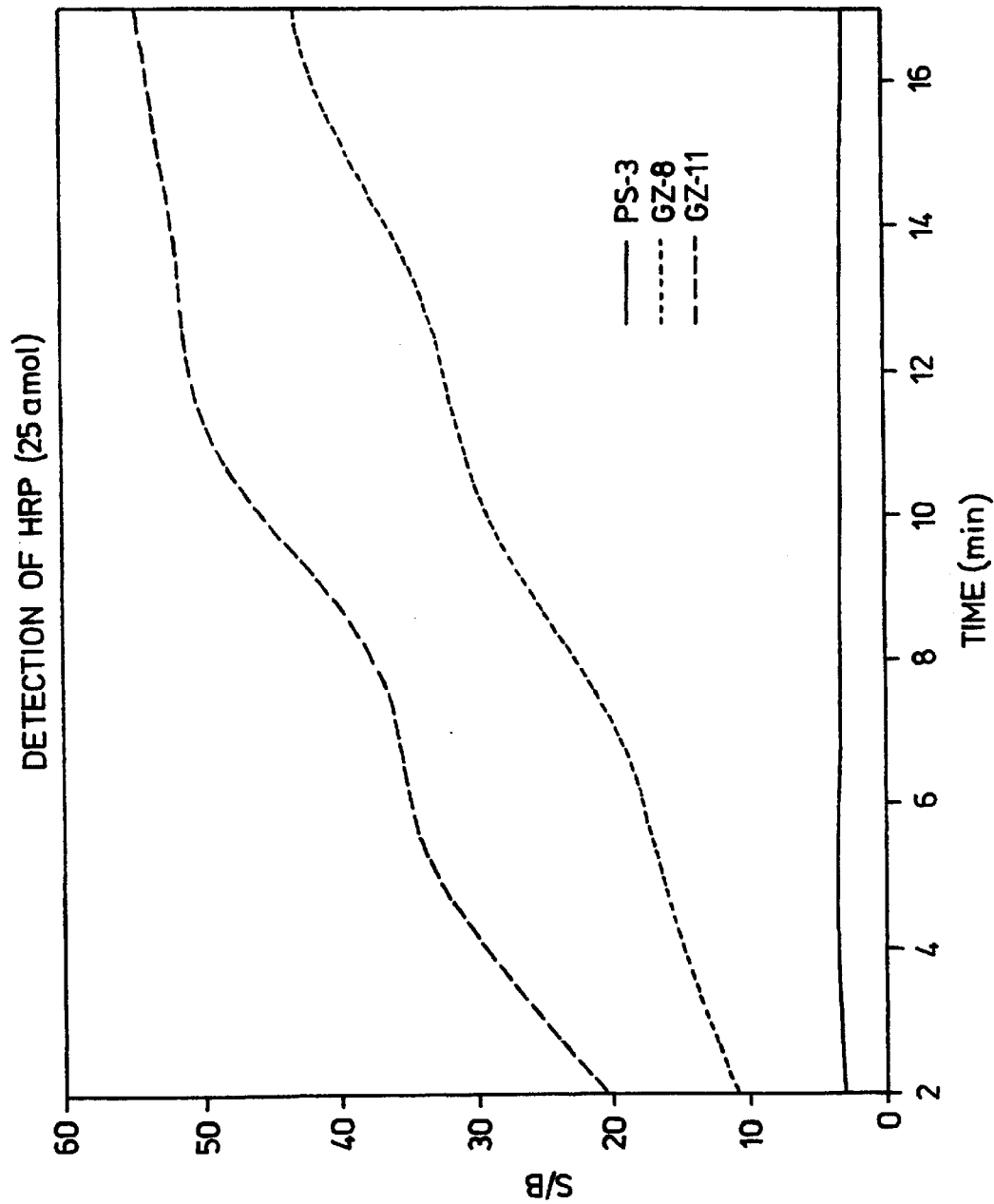

DIBENZODIHYDROPYRIDINECARBOXYLIC ESTERS AND THEIR USE IN CHEMILUMINESCENT ASSAY METHODS

The invention relates to novel dibenzodihydropyridinecarboxylic esters, in particular acridanecarboxylic esters, and to their use as a chemiluminescent substrate in peroxidase assay methods.

Aromatic acridane esters have been known for more than 20 years (McCapra, *Acc. Chem. Res.*, 1976; 9:201). The chemiluminescence of acridane esters proceeds in dipolar aprotic solvents upon addition of strong base. The mechanism is reported to involve a reaction with oxygen of the corresponding carbanion formed by the addition of the base. EP-A-625510 discloses certain aromatic acridane esters, in particular p-hydroxyphenyl 10-methylacridan-9-carboxylate, which can be used as a part of a signal reagent for the enzyme horseradish peroxidase (HRP). The signal reagent also contained an enhancer e.g. para-iodophenol, a chelating agent (EDTA), a nonionic surfactant, and hydrogen peroxide. According to EP-A-625510, HRP can be detected with great sensitivity at an optimal pH range of 8–9. More potent chemiluminescent polyfluoro-phenyl esters of acridane-9-carboxylic acid are disclosed in WO 95/23971 and phenyl thioesters are described in WO 95/28495.

The optimum pH for HRP is around pH 5. Therefore, it seems unsatisfactory that the optimum pH for chemiluminescence detection of HRP is at pH 8–9. This pH is presumably a compromise between the best pH for the for the enzyme and the optimal pH for intermediate acridinium ester chemiluminescence, which occurs at basic pH's (Akhavan-Tafti et al. in: *Bioluminescence and Chemiluminescence. Fundamentals and Applied Aspect. Proceedings of the 8th International Symposium on Bioluminescence and Chemiluminescence*. Cambridge, September 1994. Ed. Campbell, Kricka, Stanley. John Wiley and Sons 1994:199).

The present invention aims at an enzyme assay and at reagents to be used therein, which allow a higher sensitivity than the assay and reagents of the prior art. The present invention is based on the surprising discovery that certain aliphatic acridane esters and phenanthridane esters are capable of very intense and prolonged chemiluminescence upon reaction with hydrogen peroxide and certain enhancers. This reaction proceeds over a wide pH range (optimum pH range 6–8), and without the necessity of adding chelating compounds (EDTA) or surfactants. Moreover, these aliphatic esters produce a very low background luminescence, i.e. without enzyme.

Thus the invention is concerned with dibenzodihydropyridinecarboxylic ester having formula 1 or 2:

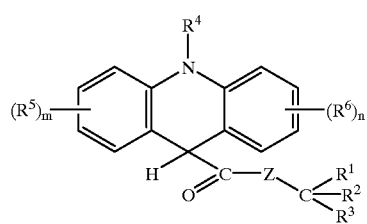

1

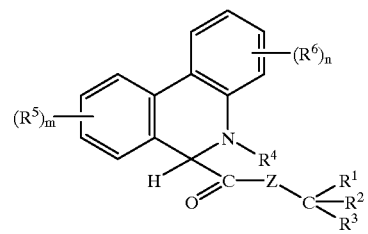

2 wherein:
$R^1$ is substituted alkyl or cyano:
$R^2$ and $R^3$ are independently selected from hydrogen, alkyl, substituted alkyl, aryl and substituted aryl;
$R^4$ is selected from hydrogen, alkyl, substituted alkyl, aryl and substituted aryl;
$R^5$ and $R^6$ are independently selected from alkyl, alkoxy, halogen, and other substituents which are relatively resistant to oxidation:
m and n are integers from 0 and 4; wherein, if m or n is at least 2, two groups $R^5$ or $R^6$ may be bound together; and
Z is oxygen or sulphur.

The dibenzodihydropyridinecarboxylic esters according to the invention can be acridane-9-carboxylic esters having formula 1, or phenanthridane-6-carboxylic esters having formula 2.

A key feature of the compounds according to the invention is that the α-carbon atom of the ester alkyl group is an aliphatic carbon atom. It may be substituted with various aliphatic or other groups, designated in the above formulae 1 and 2 by $R^1$, $R^2$ and $R^3$.

In the specification of the compounds according to the present invention, "alkyl" means straight or branched, saturated or unsaturated $C_1$–$C_{24}$, preferably $C_1$–$C_{12}$, most preferably $C_1$–$C_4$ alkyl, such as methyl, ethyl, propyl, isopropyl, butyl and decyl. "Substituted alkyl" means alkyl as defined above containing one or more substituents such as halogen, hydroxy, alkoxy, alkanoyl, carboxyl, alkoxycarbonyl, alkanoyloxy, aryl, aryloxy, aroyl, aroyloxy, cyano, nitro and the like, especially halogen, hydroxy, alkoxy and aryl; the substituents themselves may also be substituted, e.g. with halogen, alkyl or alkoxy. "Aryl" means phenyl, naphthyl and higher carbocyclic aryl, as well as hetero-aryl such as furyl, thienyl, pyrrolyl, imidazolyl, thiazolyl, oxazolyl, pyridyl, pyrimidyl, quinolyl and the like. "Substituted aryl" means aryl as defined above containing one or more substituents as exemplified above for substituted alkyl; examples include chlorophenyl, trifluoromethylphenyl, methoxyphenyl, methylenedioxyphenyl and hydroxypyridyl. In "alkoxy", the alkyl part may be as defined above; examples include methoxy, ethoxy, t-butoxy, 2-chloroethoxy, 2-methoxyethoxy, hexafluoroisopropoxy, benzyloxy, 2-phenylethoxy and the like.

Substituents which are relatively resistant to oxidation are understood to comprise substituents that do not interfere with the enzymatic oxidation process, such as halogen, alkyl, haloalkyl, hydroxyalkyl, alkoxyalkyl, alkoxy, carboxyl, alkoxycarbonyl, alkanoyl, alkanoyloxy, cyano, nitro, carbamoyl, acylamino, sulpho, phospho, phenyl, pyridyl and other aryl groups, and the like.

Preferably, at least one of $R^1$, $R^2$ and $R^3$ is a group containing electron-with-drawing substituents such as halogen, nitro, sulpho, cyano, acyl, sulphonyl, carboxyl. A suitable group with electron-withdrawing substituents is haloalkyl, such as mono-, di- and trichloromethyl, mono-, di- and trifluoromethyl, tri- or pentafluoroethyl, heptafluoropropyl and higher homologues. Especially preferred are trifluoromethyl groups for $R^1$ and optionally also for $R^2$, $R^3$ may then be e.g. hydrogen, lower alkyl, haloalkyl, phenyl or halophenyl. $R^1$ may also be cyano, in which case $R^2$ may be e.g. hydrogen, methyl, phenyl or trifluoromethyl and $R^3$ e.g. hydrogen.

The nature of the substituent represented by $R^4$ is not very critical. For reasons of convenience, $R^4$ may be lower alkyl, especially methyl, but it may also be e.g. hydrogen, substituted alkyl (examples: carboxymethyl, hydroxyethyl, benzyl), phenyl or substituted phenyl.

The substituents $R^5$ and $R^6$ are preferably attached to the m- and/or p-positions with respect to the ring nitrogen, most preferably in the p-positions. Combinations of substituents $R^5$ or $R^6$ (m or n being a number of 2 or higher) that may be bound together include $C_1$–$C_6$ alkylene and other bivalent groups that, together with the benzo groups to which they are attached, form an additional ring such as cyclopenta $((R^5)_2$=$(CH_2)_3)$, cyclohexa $((R^5)_2$=$(CH_2)_4)$, furo $((R^5)_2$=$CH_2$—O—$CH_2)$, dioxolo $((R^5)_2$=O—$CH_2$—O), benzo $((R^5)_2$=CH=CH—CH=CH), pyrido $((R^5)_2$=N=CH—CH=CH or CH=N—CH=CH), and the like. Preferred groups $R^5$ and/or $R^6$ are chloro, fluoro, bromo, methoxy, methylenedioxy, most preferred group $R^5$ is chloro.

The dibenzodihydropyridinecarboxylic esters according to the invention can be prepared by methods known per se. A general synthesis scheme for the acridane esters, which is further illustrated in the example, can be as follows:

A suitably substituted aniline (I) having the formula $(R^5)_mC_6H_{(5-m)}NH_2$ is converted to the acetanilide (II), which is reacted with a suitably substituted phenyl bromide (III) having the formula $(R^6)_nC_6H_{(5-n)}Br$ in the presence of copper iodide to produce the diphenylamine (IV) is converted to the acridine-9-carboxylic acid (V) by reaction with oxalic chloride in the presence of a Lewis acid. After esterification with the appropriate alcohol $R^1R^2R^3COH$ or thiol $R^1R^2R^3CSH$ and N-alkylation, the 9-alkoxy-carbonyl- or 9-alkylthiocarbonyl-acridinium compound with formula 3 is obtained, which can then be reduced to produce the desired acridane ester having formula 1.

The synthesis of the phenanthridane esters proceeds in an analogous way starting with optionally substituted 2-aminobiphenyl. Acetylation and ring closure yields (substituted) 5-methylphenanthridine. The 6-carboxy group is introduced by reaction of (substituted) 5-methylphenanthridine with formaldehyde, followed by oxidation to give (substituted) 6-carboxy-5-methylphenanthridine. Esterification with the appropriate alcohol or thiol, followed by N-alkylation yields the 6-alkoxycarbonyl- or 6-alkyl-thiocarbonyl-phenanthridinium compound with formula 4.

The invention furthermore relates to a method for assaying a peroxidase, wherein a dibenzodihydropyridinecarboxylic ester as described above is used as a chemiluminescent substrate. The method can be used for assaying the peroxidase enzyme itself, or for assaying an analyte labelled with the peroxidase. The method is extremely sensitive in that peroxidase levels as low as $10^{-20}$ moles can be reliably detected.

In the method of the invention, the dibenzodihydropyridinecarboxylic ester according to the invention is contacted with a sample containing the peroxidase or the analyte labelled with the peroxidase, and with a peroxide and optionally an enhancer so as to generate light. The light is most probably generated by an excited state of the dihydropyridone resulting from the reaction with peroxide. The preferred peroxidase is horseradish peroxidase (HRP). The preferred peroxide is hydrogen peroxide; other suitable peroxides include urea peroxide, perborates and the like. The preferred enhancer is p-phenylphenol, but other phenolic enhancers such as p-iodophenol, p-thiazolyl-phenol, p-hydroxycinnamic acid, other substituted phenols and optionally substituted naphthols, hydroxy-benzothiazoles, hydroxy-benzoxazoles and hydroxy-fluorenones, can also be used. The pH to be used in the method of the invention can vary over a wide range, for example from 4 to 10. The preferred pH range is from 5.5 to 8, in particular from 6 to 7.5. The method is preferably performed in a buffered aqueous system. The dibenzodihydropyridinecarboxylic ester may be used in a concentration of $10^{-7}$ to $10^{-4}$ molar, the enhancer in a similar or somewhat higher concentration (e.g. $10^{-7}$ to $10^{-3}$ molar). The peroxide may be added in a concentration of e.g. $10^{-5}$ to $10^{-2}$. The enzyme may be present in the attomol ($10^{-18}$ mole) range or even lower. The presence of surfactants such as poly(ethylene oxides) or chelating agents such as EDTA is not necessary, and is therefore preferably dispensed with.

The method of the invention can also be used to assay peroxides such as hydrogen peroxide which may be generated by the action of dehydrogenase or oxidase enzymes in solution, or to assay molecular oxygen in a solution in an aprotic solvent such as acetonitrile, nitromethane, dimethyl sulphoxide and the like.

The method of the invention can further be used for assaying hydrolytic enzymes such as phosphatases and glycosidases by using a phosphorylated or glycosylated phenol which, after hydrolytic cleavage of the phosphate or glycosyl group, serves as an enhancer in a peroxidase reaction.

The invention also relates to a kit for assaying peroxidase activity comprising a dibenzodihydropyridinecarboxylic ester as described above and optionally a peroxide, a phenolic enhancer and/or further constituents for performing the assay as described above. The kit may further contain an analyte, such as an antibody, labelled with a peroxidase enzyme such as HRP. If used for peroxide detection, the kit may also contain a peroxidase as such.

The invention also relates to novel dibenzopyridinium (acridinium and phenanthridinium) compounds having formula 3 or 4:

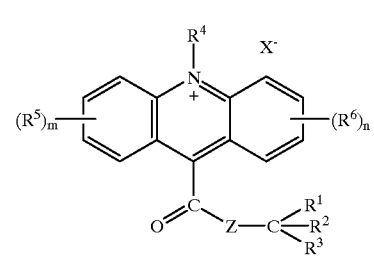

3

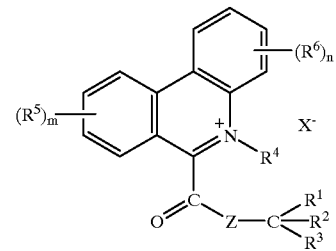

4 wherein $R^1$ and $R^6$ and Z are as defined above for compounds 1 and 2. The counterion $X^-$ may be any suitable, relatively inert ion, such as halide, sulphate, $R^7$-sulphonate wherein $R^7$ is e.g. alkyl, haloalkyl or aryl, tetrafluoroborate etc. Preferably $R^1$ is trifluoromethyl or cyano, $R^2$ is trifluoromethyl and $R^3$ is hydrogen, trifluoromethyl, phenyl or substituted phenyl. $R^5$ and/or $R^6$ are preferably halogen or methoxy, and m and n are preferably 0, 1 or 2, most preferably at least one of them is 1.

The dihydropyridinium salts can be used as a direct label for detecting the presence of analytes such as antibodies, antigens, DNA-probes and other biologically interesting substances as described in EP-A-324202. Suitable compounds 3 and 4 have substituents containing a moiety capable of chemically reacting with (bio)molecules. Examples thereof are carboxy, aldehyde, alcohol, amino or thiol functions that can be present in any one of $R^1$ or $R^6$, especially in $R^4$, such as when $R^4$ is carboxymethyl.

EXAMPLES

Synthesis of the Acridan Derivatives GZ-1GZ-12.

The compounds given in table 1 were synthesised.

The general synthesis procedure was as follows:

Acetanilide (II):

The particular aromatic amine 1 (20 g), acetic acid anhydride (20 ml), acetic acid (glacial, 20 ml) and zinc powder (0.1 g) were mixed and refluxed. After 30 min. the solution was poured into 500 ml ice water and the precipitate was filtered and dried to obtain the acetanilide.

Diphenyl amine (IV):

The acetanilide II (13.5 g), the particular aromatic bromide III (25 g), potassium carbonate (13.2 g) and copper iodide (1.9 g) were heated (190° C.) and stirred overnight. After cooling to room temperature toluene was added and the precipitate filtered. The solution was concentrated and the excess of bromide removed by distillation under reduced pressure. The residue was dissolved in ethanol (200 ml), potassium hydroxide (10.3 g) was added and the mixture refluxed overnight. Ethanol was evaporated, the residue dissolved in dichloromethane, and washed with brine. The organic layer was dried over $MgSO_4$ and concentrated to obtain the crude diphenyl amine.

TABLE 1

|  | $R^1$ | $R^2$ | $R^3$ | $R^4$ | $R^5, R^6$ | Z |
|---|---|---|---|---|---|---|
| GZ-1 | $CF_3$ | $CF_3$ | H | $CH_3$ | — | O |
| GZ-2 | $CF_3$ | $CF_3$ | H | $CH_3$ | 2-$OCH_3$, 7-$OCH_3$ | O |
| GZ-3 | $CF_3$ | $CF_3$ | H | $CH_3$ | 2-$OCH_3$, 3-$OCH_3$ | O |
| GZ-4 | $CF_3$ | $CF_3$ | H | $CH_3$ | 2-F | O |
| GZ-5 | $CF_3$ | $CF_3$ | H | $CH_3$ | 2-Cl | O |
| GZ-6 | $CF_3$ | $CF_3$ | H | $CH_3$ | 2-$OCH_3$, 6-$OCH_3$, 3-$OCH_3$, 7-$OCH_3$ | O |
| GZ-7 | $CF_3$ | $CF_3$ | H | $CH_3$ | 2-Br, 7-Br | O |
| GZ-8 | $CF_3$ | $CF_3$ | $C_6H_5$ | $CH_3$ | 2-Cl | O |
| GZ-9 | $CF_3$ | $CF_3$ | $C_6H_5$ | $CH_3$ | 2-$OCH_3$, 3-$OCH_3$ | O |
| GZ-10 | $CF_3$ | $CF_3$ | H | $CH_3$ | 3-$OCH_3$ | O |
| GZ-11 | $CF_3$ | $CF_3$ | $CF_3$ | $CH_3$ | 2-Cl | O |
| GZ-12 | $CF_3$ | H | H | $CH_3$ | — | S |

Acridine-9-carboxylic acid (GW):

To a solution of oxalic chloride (5 g) in dichloromethane, a solution of the diphenyl amine IV (5 g) in dichloromethane was added dropwise and refluxed for 30 min. The solution was concentrated (50%) and aluminium trichloride (8 g) added in portions. The mixture was refluxed for 45 min. and the solvent evaporated. To this residue hydrochloric acid in ice water (1 molar) was added and the red coloured precipitate filtered. The precipitate was dissolved in potassium hydroxide (10% in water), refluxed overnight and poured into hydrochloric acid in ice water (5 molar). The yellow acridine-9-carboxylic acid (GW) was filtered, washed with water and dried.

Acridine-9-carboxylic ester (GX):

The acridine-9-carboxylic acid GW (1 g) was mixed with thionyl chloride (20 ml) and refluxed until a clear solution was obtained. The solution was concentrated and the excess thionyl chloride coevaporated with toluene. To the residue pyridine (20 ml), dimethylaminopyridine (1 g) and an excess of the particular alcohol (or thiol) $R^1R^2R^3$COH(—SH) were added. The mixture was stirred overnight at room temperature, poured into hydrochloric acid in ice water (1 molar) and extracted with dichloromethane. The organic layer was washed with water, dried over $MgSO_4$ and concentrated. The crude product was purified by flash-chromatography (66% hexanes/ethyl acetate).

10-Methylacridinium-9-carboxylic ester trifluoromethanesulfonate (GY):

The acridine-9-carboxylic ester GX (100 mg) was dissolved in dichloromethane (5 ml). to this solution an excess of methyl trifluoromethanesulfonate was added. The mixture was stirred overnight at room temperature. Diethyl ether was added and the obtained precipitate was filtered, washed with diethyl ether and dried.

10-Methylacridane-9-carboxylate (GZ):

The 10-methylacridinium-9-carboxylic ester trifluoromethanesulfonate GY (100 mg) was dissolved in dichloromethane (100 ml). To this solution perchloric acid (20 drops) and zinc powder (6 g) were added. The mixture was placed in an ultrasone bath for three hours and filtered. The solution was washed with water (1x) and hydrochloric acid (2x, 0.1 molar), dried over $MgSO_4$ and concentrated.

Example 1

Synthesis of GZ-1

Hexafluoroisopropyl acridine-9-carboxylate (GX-1)
$^1$H NMR (acetone-$d_6$)δ7.2 (m, 1H), 7.8–8.3 (m, 8H).
9-Hexafluoroisopropoxycarbonyl-10-methylacridinium trifluoromethanesulfonate (GY-1)
$^1$H NMR (acetone-$d_6$)δ5.3 (s, 3H), 7.4 (m, 1H), 8.2–9.2 (m, 8H).
$^{13}$C NMR (acetone-$d_6$)δ38.3, 41.4, 70.4, 120.5, 121.6, 124.2, 125.3, 127.8, 131.6, 141.2, 144.1, 146.4, 149.4, 163.4, 165.2.
Hexafluoroisopropyl 10-methylacridane-9-carboxylate (GZ-1)
$^1$H NMR (acetone-$d_6$)δ3.5 (s, 3H), 5.4 (s, 1H) 6.2 (m, 1H), 6.9–7.4 (m, 8H).

Example 2

Synthesis of GZ-2

2,7-Dimethoxyacridine-9-carboxylic acid (GW-2)
$^1$H NMR (acetone-$d_6$)δ4.0 (s, 6H), 7.1–8.2 (m, 6H)
Hexafluoroisopropyl 2,7-dimethoxyacridine-9-carboxylate (GX-2)
$^1$H NMR ($CDCl_3$)δ4.0 (s, 6H), 6.4 (m, 1H), 7.0–8.1 (m, 6H).
9-Hexafluoroisopropyoxycarbonyl-2,7-dimethoxy-10-methylacridinium trifluoromethanesulfonate (GY-2)
$^1$H NMR (acetone-$d_6$)δ4.1 (s, 6H), 5.2 (s, 3H), 7.2 (d, 2H-acr), 7.3 (m, 1H), 8.1 (dd, 2H-acr), 9.0 (d, 2H-acr).
Hexafluoroisopropyl 2,7-dimethoxy-10-methylacridane-9-carboxylate (GZ-2)

¹H NMR (acetone-d₆)δ3.4 (s, 3H), 3.7 (s, 6H), 5.3 (s, 1H), 6.2 (m, 1H), 6.8–7.0 (m, 6H).

Example 3

Synthesis of GZ-3

2,3-Dimethoxyacridine-9-carboxylic acid (GW-3)
¹H NMR (DMSO-d₆)δ3.9 (s, 3H), 4.0 (s, 3H), 7.2–8.1 (m, 6H).
Hexafluoroisopropyl-2,3-dimethoxyacridine-9-carboxylate (GX-3)
¹H NMR (acetone-d₆)δ4.0 (s, 3H), 4.1 (s, 3H), 7.1 (s, 1H-acr), 7.2 (m, 1H), 7.5–8.2 (m, 5H-acr).
9-Hexafluoroisopropoxycarbonyl-2,3-dimethoxy-10-methylacridinium trifluoromethanesulfonate (GY-3)
¹H NMR (acetone-d₆)δ4.2 (s, 3H), 4.4 (s, 3H), 5.1 (s, 3H), 7.3 (s, 1H-acr), 7.4 (m, 1H), 8.1–8.9 (m, 5H-acr).
Hexafluoroisopropyl 2,3-dimethoxy-10-methylacridane-9-carboxylate (GZ-3)
¹H NMR (acetone-d₆)δ3.5 (s, 3H), 3.8 (s, 3H), 3.9 (s, 3H), 5.3 (s, 1H), 6.2 (m, 1H), 6.8–7.3 (m, 6H).

Example 4

Synthesis of GZ-4

2-Fluoroacridine-9-carboxylic acid (GW-4)
¹H NMR (CDCl₃)δ7.7–8.4 (m,7H)
Hexafluoroisopropyl 2-fluoroacridine-9-carboxylate (GX-4)
¹H NMR (CDCl₃)δ6.3 (m, 1H), 7.5–8.4 (m, 7H)
¹³C NMR (CDCl₃)δ67.5 (m), 106.5 (d), 118.3, 122.4 (d), 122.5 (d), 122.9, 123.7, 128.9, 130.4 (d), 133.3 (d), 146.0, 148.0 (d), 159.4, 163.1, 164.2.
9-Hexafluoroisopropoxycarbonyl-2-fluoro-10-methylacridinium trifluoromethane-sulfonate (GY-4)
¹H NMR (acetone-d₆)δ5.3 (s, 3H), 7.3 (m, 1H), 7.9–9.3 (m, 7H).
Hexafluoroisopropyl 2-fluoro-10-methylacridane-9-carboxylate (GZ-4)
¹H NMR (CDCl₃)δ3.4 (s, 3H), 5.1 (s, 1H), 5.5 (m, 1H) 6.9–7.4 (m, 7H)
¹³C NMR (CDCl₃)δ33.4 (d), 48.8 (d), 76.3 (m), 112.9, 113.8 (d), 115.4 (2xd), 118.0, 119.9, 120.0, 121.0 (q), 122.2, 128.9 (d), 138.8, 142.2 155.8, 159.3, 168.0.

Example 5

Synthesis of GZ-5

2-Chloroacridine-9-carboxylic acid (GW-5)
¹H NMR (CDCl₃)δ7.7–18.3 (m, 7H).
Hexafluoroisopropyl 2-chloroacridine-9-carboxylate (GX-5)
¹H NMR (CDCl₃)δ6.3 (m, 1H), 7.7–8.3 (m, 7H).
¹³C NMR (CDCl₃)δ67.6 (m), 118.3, 122.6, 124.0, 128.9, 130.5, 130.8, 131.6, 131.9, 146.8, 148.6, 164.1.
9-Hexafluoroisopropoxycarbonyl-2-chloro-10-methylacridinium trifluoromethane-sulfonate (GY-5)
¹H NMR (acetone-d₆)δ5.3 (s, 3H), 7.4 (m, 1H), 8.3–9.2 (m, 7H).
Hexafluoroisopropyl 2-chloro-10-methylacridane-9-carboxylate (GZ-5)
¹H NMR (acetone-d₆)δ3.4 (s, 3H), 5.5 (s, 1H), 6.2 (m, 1H), 7.0–7.5 (m, 7H).

Example 6

Synthesis of GZ-6

2,3,6,7-Tetramethoxyacridine-9-carboxylic acid (GW-6)
¹H NMR (DMSO-d₆)δ3.8 (s, 6H), 3.9 (s, 6H), 7.3 (s, 2H), 7.4 (s,2H).
Hexafluoroisopropyl 2,3,6,7-tretramethoxyacridine-9-carboxylate (GX-6)
¹H NMR (CDCl₃)δ4.0 (s, 6H), 4.1 (s, 6H), 6.4 (m, 1H), 7.1 (s, 2H), 7.5 (s, 2H).
9-Hexafluoroisopropoxycarbonyl-2,3,6,7-tetramethoxy-10-methylacridinium trifluoromethanesulfonate (GY-6)
¹H NMR (acetone-d₆)δ4.1 (s, 6H), 4.3 (s, 6H), 5.0 (s, 3H), 7.2 (s, 2H), 7.3 (m, 1H), 8.1 (s, 2H).

Example 7

Synthesis of GZ-8

α,α-Bis(trifluoromethyl)benzyl 2-chloroacridine-9-carboxylate (GX-8)
¹H NMR (CDCl₃)δ7.5–8.3 (m, 12H).
9-[α,α-Bis(trifluoromethyl)benzyloxycarbonyl]-2-chloro-10-methylacridinium trifluoromethanesulfonate (GY-8)
¹H NMR (acetone-d₆)δ5.3 (s, 3H), 7.1–9.3 (m, 12H).
α,α-Bis(trifluoromethyl)benzyl 2-chloro-10-methylacridane-9-carboxylate (GZ-8)
¹H NMR (CDCl₃)δ3.39 (s, 3H), 5.07 (s, 1H), 6.8–7.4 (m, 12H)
¹³C NMR (CDCl₃)δ165.6, 141.8, 140.9, 129.9, 129.2, 129.0, 128.7, 128.5, 128.2, 127.8, 126.8, 126.3, 126.0, 125.7, 123.5, 121.1, 120.6, 119.3, 118.5, 115.0, 114.5, 114.0, 112.9, 49.8, 33.2

Example 8

Synthesis of GZ-9

α,α-Bis(trifluoromethyl)benzyl 2,3-dimethoxyacridine-9-carboxylate (GX-9)
¹H NMR (CDCl₃)δ4.0 (s, 3H), 4.1 (s, 3H), 7.5–8.2 (m, 11H).
9-[α,α-Bis(trifluoromethyl)benzyloxycarbonyl]-2,3-dimethoxy-10-methylacridinium trifluoromethane-sulfonate (GY-9)
¹H NMR (acetone-d₆)δ4.1 (s, 3H), 4.4 (s, 3H), 5.1 (s, 3H), 7.5–8.9 (m, 11H).

Example 9

Synthesis of GZ-10

Hexafluoroisopropyl 3-methoxyacridine-9-carboxylate (GX-10)
¹H NMR (CDCl₃)δ4.0 (s, 3H), 6.3 (m, 1H), 7.3–8.2 (m, 7H).
9-Hexafluoroisopropoxycarbonyl-3-methoxy-10-methylacridiniumtrifluoromethane-sulfonate (GY-10)
¹H NMR (acetone-d₆)δ4.4 (s, 3H), 5.0 (s, 3H), 7.3 (m, 1H), 7.7–9.0 (m, 7H).

Example 10

Synthesis of GZ-11

Perfluoro-t-butyl 2-chloroacridine-9-carboxylate (GX-11)
¹H NMR (CDCl₃)δ7.6–7.9 (m, 5H), 8.2–8.3 (m, 2H).
9-Perfluoro-t-butoxycarbonyl-2-chloro-10-methylacridinium trifluoromethane-sulfonate (GY-11)

¹H NMR (acetone-d₆)δ5.3 (s, 3H), 8.2–9.3 (m, 7H).
Perfluoro-t-butyl 2-chloro-10-methylacridane-9-carboxylate (GZ-11)
¹H NMR (CDCl₃)δ3.4 (s, 3H), 5.1 (s, 1H), 6.9–7.4 (m, 7H).
¹³C NMR (CDCl3δ163.9, 141.7, 140.8, 129.3, 128.9, 128.5, 125.7, 121.4, 121.2, 119.7, 117.8, 117.1, 114.0, 113.0, 49.5, 33.1

Example 11

Chemiluminescence Measurements using GZ-8.

Chemiluminescence (CL) measurements were performed in lumacuvettes using a Lumac Biocounter M2010. A chemiluminogenic signal reagent consisted of a solution of phenylphenol (9*10⁻⁵ M), GZ-8 (4*10⁻⁶ M) in PBS buffer (pH 7.2, 0.01 M). To this solution was added 250 attomoles of HRP. The lumacuvette was placed in the luminometer and the CL reaction was started by the addition of hydrogen peroxide (4*10⁻⁴ M). The CL reaction was followed over a period of 22 minutes. The resulting CL kinetic profile is shown in FIG. 1.

Example 12

HRP Calibration Curve using GZ-8.

Figure 2:
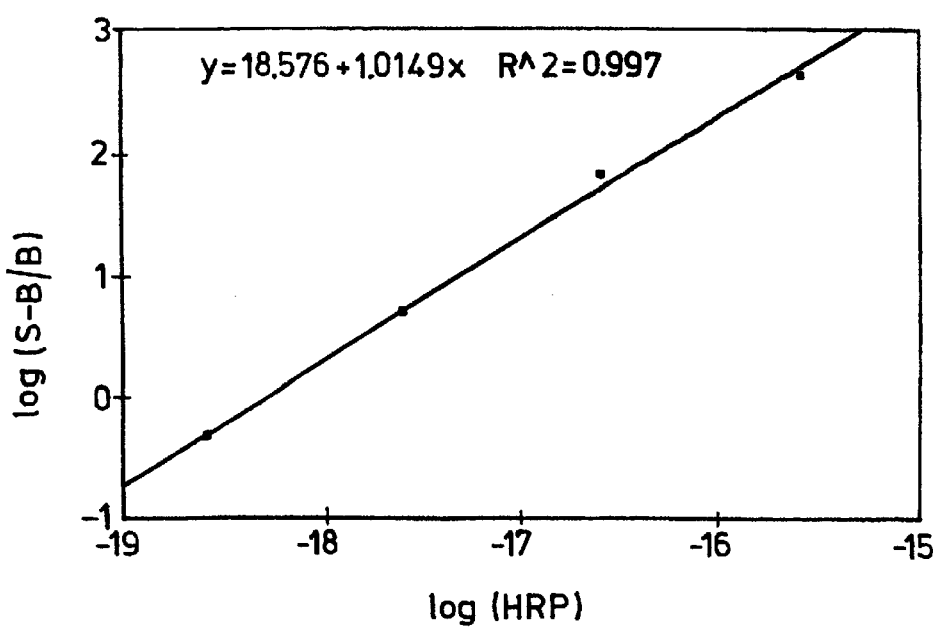

In a similar experiment as described in example 12, different amounts of HRP (0–250 amol) were incubated with phenylphenol (9*10⁻⁵ M), GZ-8 (4*10⁻⁶ M) in PBS buffer (pH 7.2, 0.01 M). To all the tubes was added hydrogen peroxide (4*10¹⁰⁻⁴ M). After 16 minutes the CL was measured. The CL-counts, corrected for background, were plotted against the amounts of HRP to obtain a HRP calibration curve. An example of such a calibration curve is shown in FIG. 2.

Example 13

Chemiluminescent Measurements using GZ-11

Figure 3:
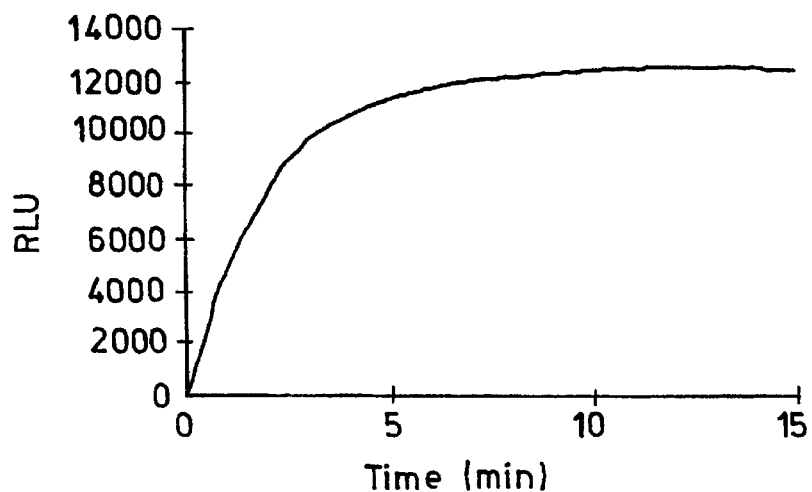

In a similar experiment as described in example 12, a kinetic curve for the CL-reaction of HRP (25 amol) with GZ-11 was constructed. The results are shown in FIG. 3. When comparing FIGS. 1 and 3, it can be seen that the use of GZ-11 as part of the CL-signal reagent causes a much more rapid rise of the CL with time. Within 2 minutes the curve reaches half of the maximal value. The results are shown in FIG. 3.

Example 14

HRP Calibration Curve using GZ-11

Figure 4:
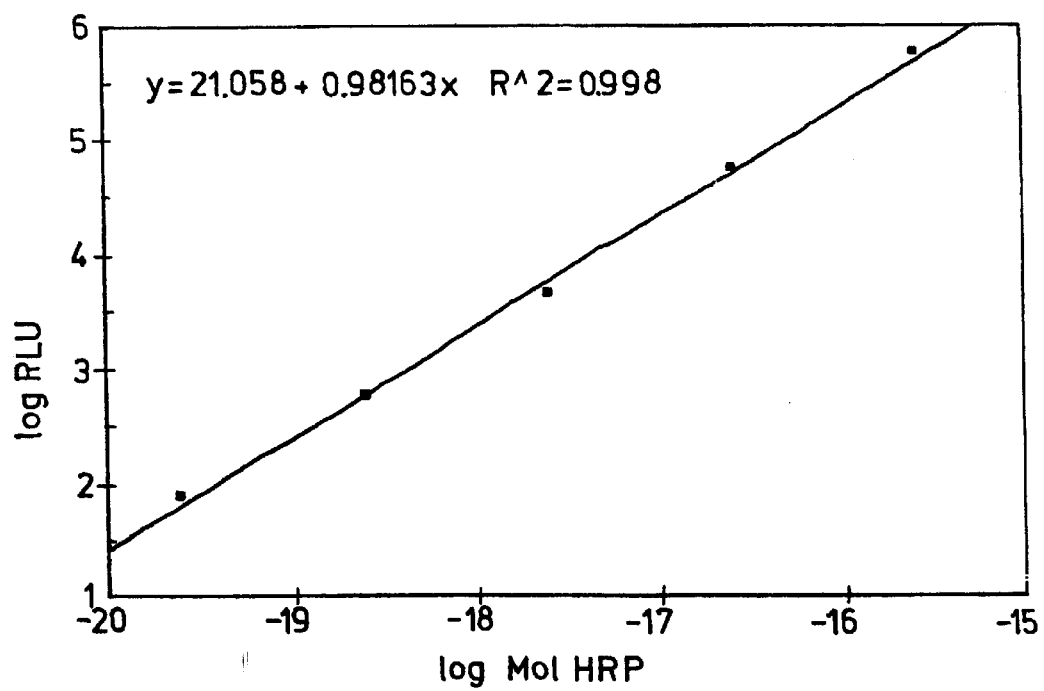

A HRP calibration curve was constructed using the same procedure as described in example 13. This gave the calibration curve as shown in FIG. 4.

Example 15

Comparison of Chemiluminescence of GZ-8 and GZ-11 with Prior Art Compound

Compound 5 c of WO95/23971 (2,3,6-trifluorophenyl 10-methylacridan-9-carboxylate, also denoted as Lumigen PS-3) was synthesized according to the general synthesis procedure starting from 9-acridinecarboxylic acid and 2,3,6-trifluorophenol.
¹H NMR (CDCl₃): 3.44 (s, 3H), 5.29 (s, 1H), 6.76–7.4 (m, 10H).

The CL measurements of GZ-8 and GZ-11 were performed as described in examples 12 and 14, respectively, using 25 amol of HRP for GZ-8 as well.

The CL measurements of PS-3 were performed using a signal reagent containing PS-3 (0.05 mM), para-iodophenol (1.1 mM). Tween 20 (0.5%), EDTA (1 mM) and $H_2O_2$ (0.4 mM) in Tris buffer (0.1 M, pH 8). Upon addition of 25 amol of HRP, the CL was recorded over a period of 17 minutes. The results are shown in FIG. 5, wherein S/B denote signal to background ratio.

We claim:

1. Dibenzodihydropyridinecarboxylic ester having formula 1 or 2, wherein:

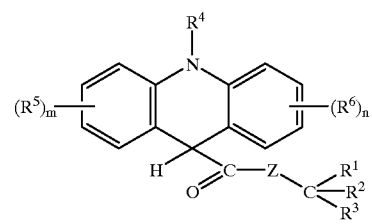

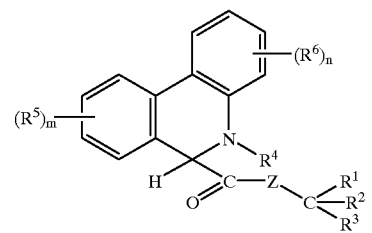

$R^1$ is alkyl substituted by halogen, nitro, sulpho, cyano, acyl, sulphonyl or carboxyl, or $R^1$ is cyano;

$R^2$, $R^3$ and $R^4$ are independently hydrogen, alkyl, aryl, or alkyl or aryl substituted by halogen, hydroxy, alkoxy, alkanoyl, carboxyl, alkoxycarbonyl, alkanoyloxy, aryl, aryloxy, aroyl, aroyloxy, cyano or nitro;

$R^5$ and $R^6$ are independently halogen, alkyl, haloalkyl, hydroxyalkyl, alkoxyalkyl, alkoxy, carboxyl, alkoxycarbonyl, alkanoyl, alkanoyloxy, cyano, nitro, carbamoyl, acylamino, sulpho, phospho, phenyl, pyridyl or other aryl;

m and n are integers from 0 to 4; wherein, if m or n is at least 2, two groups $R^5$ or $R^6$ may be linked together; and Z is oxygen or sulphur.

2. Dibenzodihydropyridinecarboxylic ester according to claim 1, wherein $R^1$ is a haloalkyl group.

3. Dibenzodihydropyridinecarboxylic ester according to claim 2, wherein $R^1$ is a trifluoromethyl group.

4. Dibenzodihydropyridinecarboxylic ester according to claim 2, wherein $R^2$ is a haloalkyl group, especially a trifluoromethyl group.

5. Dibenzodihydropyridinecarboxylic ester according to any one of claim 1, wherein $R^3$ is hydrogen, alkyl, haloalkyl, phenyl or halophenyl.

6. Dibenzodihydropyridinecarboxylic ester according to any one of claim 1, wherein $R^5$ and $R^6$ are independently methoxy, chloro and/or fluoro, and m and n are independently 0 or 1.

7. Dibenzodihydropyridinecarboxylic ester according to any one of claim 1, wherein Z is oxygen.

8. A method for assaying a peroxidase, wherein a dibenzodihydropyridinecarboxylic ester according to any one of claim 1 is used as a chemiluminescent substrate.

9. The method according to claim 8, wherein a pH of 6–7.5 is used.

10. The method according to claim 8, wherein a phenol, in particular p-phenyl-phenol, is used as an enhancer.

11. A kit for assaying peroxidase activity, comprising a dibenzodihydropyridine-carboxylic ester according to any one of claim 1, and optionally a peroxide, a phenolic enhancer, and optionally comprising a peroxidase.

12. Dibenzopyridinium compound having formula 3 or 4,

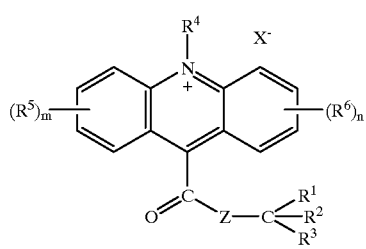

3

-continued

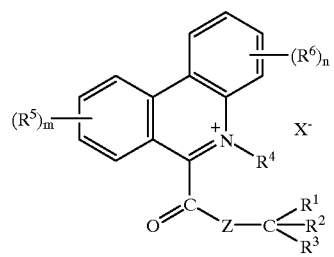

4 wherein $R^1$ is haloalkyl or cyano;

$R^2$, $R^3$ and $R^4$ are independently hydrogen, alkyl, aryl, or alkyl or aryl substituted by halogen, hydroxy, alkoxy, alkanoyl, carboxyl, alkoxycarbonyl, alkanoyloxy, aryl, aryloxy, aroyl, aroyloxy, cyano or nitro;

$R^5$ and $R^6$ are independently halogen, alkyl, haloalkyl, hydroxyalkyl, alkoxyalkyl, alkoxy, carboxyl, alkoxycarbonyl, alkanoyl, alkanoyloxy, cyano, nitro, carbamoyl, acylamino, sulpho, phospho, phenyl, pyridyl or other aryl;

m and n are integers from 0 to 4; wherein, if m or n is at least 2, two groups $R^5$ or $R^6$ may be linked together, preferably at least one of m and n being 1 or 2; and X is an inert counterion;

Z is oxygen or sulphur.

* * * * *